United States Patent [19]

Kaufman et al.

[11] Patent Number: 5,451,521
[45] Date of Patent: Sep. 19, 1995

[54] PROCOAGULANT PROTEINS

[75] Inventors: Randal J. Kaufman, Boston; Debra D. Pittman, Arlington, both of Mass.; John J. Toole, Jr., Palo Alto, Calif.

[73] Assignee: Genetics Institute, Inc., Cambridge, Mass.

[21] Appl. No.: 939,658

[22] Filed: Dec. 9, 1986

Related U.S. Application Data

[63] Continuation-in-part of Ser. No. 868,410, May 29, 1986, abandoned, and a continuation-in-part of Ser. No. 932,767, Nov. 18, 1986, abandoned.

[51] Int. Cl.$^6$ .................. A61K 38/37; C07K 14/755; C12N 5/06; C12N 15/12
[52] U.S. Cl. .................. 435/240.2; 435/252.3; 435/320.1; 514/12; 530/383; 536/23.5; 930/100
[58] Field of Search .............. 435/68, 70, 172.3, 320, 435/948, 240.2, 69.6, 320.1, 252.3; 935/10, 34, 56, 57, 70, 71; 536/27, 23.5; 530/383; 514/8, 12; 930/100

[56] References Cited

U.S. PATENT DOCUMENTS

4,518,584  5/1985  Mark et al. .......................... 424/85

OTHER PUBLICATIONS

Vehar et al *Nature* vol. 312 Nov. 22, 1984 pp. 337–342 "Structure of human factor VIII".
Wood et al *Nature* vol. 312 Nov. 22, 1984 pp. 330–336 "Expression of active human factor VIII from recombinant cDNA clones".
Toole et al *Nature* vol. 312 Nov. 22, 1984 pp. 342–347 "Molecular cloning of a cDNA encoding human antihaehophilius factor".
Norris et al *Nucl Acids Res* vol. 11 pp. 5103–5112 1983.
Orr et al *Thrombos Haemostus* vol. 54(1) pp. 54–1985 Abstract 5321.
Eaton et al Feb. 1986 *Biochem* vol. 25 pp. 505–512 "Proteolytic processing of human factor VIII correlation of specific cleavages by thrombin, factor Xa, . . . ".
Andersson et al *Proc Natl Acad Sci* vol. 83 May 1984 pp. 2979–2983 "Isolation and characterization of human factor VIII: Molecular forms in".
Burke et al *J Biol Chem* vol. 261 (27) Sep. 25, 1986 "The functional domains of coagulation factor VIII:C".

*Primary Examiner*—Keith C. Furman
*Assistant Examiner*—D. C. Jacobson
*Attorney, Agent, or Firm*—Bruce M. Collins; Thomas J. DesRosier; M. C. Meinert

[57] ABSTRACT

This invention relates to recombinant Factor VIII:c variants, methods to produce the variants and pharmaceutical compositions containing same. The variants of this invention are characterized by modification of one or more specific proteolytic cleavage sites encompassing the arginine residues at positions 226, 336, 562, 740, 776, 1313, 1648, or 1721. The variants possess similar procoagulant activity to that of human Factor VIII:c.

32 Claims, No Drawings

PROCOAGULANT PROTEINS

This application is a continuation-in-part of U.S. Ser. Nos. 868,410, and 932,767 filed May 29, 1986 and Nov. 18, 1986, respectively, both of which are now abandoned, which are hereby incorporated by reference.

Certain aspects of the research resulting in the present invention were funded in part by the U.S. Department of Health and Human Services (DHHS) under a Small Business Innovation Research (SBIR) Grant, DHSS Grant No. 1 R43 HL35946-01. The United States Government has certain rights in this invention.

This invention relates to substances having procoagulant activity. More specifically, this invention relates to "recombinant" procoagulant proteins, a process for obtaining the proteins from genetically engineered cells, and therapeutic compositions containing the proteins for use as procoagulant agents.

The characterization of human factor VIII from plasma indicates that its coagulant activity is associated with a multitude of polypeptide chains having molecular weights ranging from about 50,000 to about 210,000 daltons. In addition, upon addition of thrombin, there is a specified pattern of proteolysis which initially activates and then inactivates the factor VIII procoagulant activity. Definition of the proteolytic cleavages necessary for factor VIII activation and inactivation process is required in order to understand the structural requirements for factor VIII activity. One approach has been that of protein sequencing of specific cleavage products before and after digestion with thrombin (Eaton et al., 1986, Biochemistry 25:505; Smart et al.). This approach has been useful to map the proteolytic sites for this protease along the factor VIII molecule. We have now analyzed human recombinant factor VIII derived from a mammalian host cell system and elucidated the same cleavage sites as determined from plasma derived VIII. Our data suggest that the recombinant protein and the natural protein are folded and processed similarly, a result which could not be predicted with confidence a priori. Our data was obtained using recombinant factor VIII purified from conditioned medium from a mammalian cell line which was engineered to produce factor VIII. The recombinant protein so obtained was characterized as a complex of an approximately 200 kd polypeptide and an approximately 76 kd polypeptide. Upon digestion with thrombin, the 200 kd species yields a 90 kd species with eventual generation of a 50 and a 40 kd species. Upon thrombin digestion the 76 kd species is cleaved to a 69 kd form. The 76 kd species is also referred to elsewhere as the "80 kd" species. However, the knowledge of the precise cleavage sites has not heretofore definitively established what cleavages are necessary for activation and subsequent inactivation.

In a further aspect of the research resulting in the present invention, the approach of site-specific mutagenesis coupled with expression of the altered forms of the factor VIII DNA was used to elucidate what sites are necessary and sufficient for the activation, as well as for inactivation of the factor VIII molecule. Specific DNA sequences were changed in order to alter specific amino acids which result in the inactivation of specific cleavage sites. The analysis of the modified forms of the factor VIII cDNA is performed by producing factor VIII protein from the cloned, modified cDNA in a mammalian host cell system capable of high level expression (Kaufman, PNAS, 1985, 82:689). Our results indicated that mutation of the 90 kd or 76 kd cleavage site does not reduce procoagulant activity or thrombin activatability. The predominant species generated in the conditioned medium from the 76 kd cleavage site mutation, at least in the case of deletion variants described hereinafter, is a single chain as monitored by SDS-polyacrylamide gel electrophoresis. Mutation of the thrombin cleavage site generating the 50 and 40 kd species renders factor VIII inactive. Mutation of the proposed activated protein C cleavage site (encompassing Arg-372) at the amino terminus renders factor VIII which has increased specific activity and perhaps decreased susceptibility to proteolytic inactivation. These modified forms of factor VIII may have beneficial effects upon administration in vivo due to increased activity of a single chain molecule, decreased inactivation due to protein C inactivation, or increased half-life or specific activity.

This invention provides a family of Factor VIII:c-like proteins containing modifications relative to natural human Factor VIII:c at one or more of the sites of specific protease-catalyzed cleavage of natural human Factor VIII:c but which retain procoagulant activity and thrombin activatibility. The sites are referred to hereinafter simply as "cleavage sites" and include the cleavage site between Arg-226 and Ala-227, the "proposed activated Protein C ('APC') cleavage site" between Arg-336 and Met-337, the cleavage site between Arg-562 and Gly-563, the "90 kd cleavage site" between Arg-740 and Ser-741, the "95 kd cleavage site" between Arg-776 and Thr-777, the "115 kd cleavage site" between Arg-1313 and Ala-1314, the "76 kd cleavage site" between Arg-1648 and Glu-1649, and the "Factor Xa cleavage site" between Arg-1721 and Ala-1722. Throughout this disclosure the numbering of amino acids is with reference to the amino acid sequence of Factor VIII:c as depicted in Table 1, wherein the amino terminus of the mature protein is Ala-1.

By "Factor VIII:c-like proteins" (also referred to hereinafter as "variants"), we mean proteins characterized by an amino acid sequence substantially the same, except at one or more cleavage sites, as the amino acid sequence of natural human Factor VIII:c or of analogs thereof (hereinafter, "deletion analogs") containing deletions of 1-1317 amino acids between Ser-373 and Ser-1690, inclusive, which retain procoagulant activity.

One aspect of the invention relates to variants wherein one or both of the amino acids defining the cleavage site, preferably at least the arginine residue, is replaced by a different amino acid. The replacement may be a conservative change, e.g. the replacement of Arg with Lys, to minimize the chance of effecting a change in the secondary structure of the protein. Alternatively the change may be a non-conservative change, e.g. the replacement of Arg with Ile, to guarantee resistance to proteolysis. Compounds of this aspect of the invention thus include variants wherein arginine at one or more of positions 226, 336, 562, 740, 776, 1313, 1648, or 1721, and optionally at one or more of positions 220 ,250, 279 and 282, is replaced by an amino acid, independently selected from lysine or a non-basic amino acid such as isoleucine, for example. These variants may in addition contain lysine optionally substituted for Arg-1689 at the 69 kd cleavage site.

Another aspect of the invention relates to variants wherein a tripeptide sequence spanning the cleavage site is replaced by a consensus asparagine-linked glycosylation site. Consensus N-linked glycosylation sites comprise

TABLE I
Full-length Protein Sequence of Human Factor VIII:c

```
              Signal   50kDa
                        ↓ 1
          ***** ********** ****** ******    **     ****** ***
MQIELSTCFF LCLLRFCFSA TRRYYLCAVE LSWDYMQSDL GELPVDARFP PRVPKSFPFN TSVVYKKTLF VEFTMHLFNI AKPRPPWMGL LGPTIQAEVY

*  ***** **                                                          101
DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE
                                                                           201
                       ***
GSLAKEKTQT LHKFILLFAV FDEGKSWHSE TKNSLMQDRD AASARAWPKM HTVNGYVNRS LPGLIGCHRK SVYWHVIGMG TTPEVHSIFL ECHTFLVRNH
                                                                           301
                                                                                                    494kDa
                                                                                                 *********
RQASLEISPI TFLTAQTLLM DLGQFLLFCH ISSHQHDGME AYVKVDSCPE EPQLRMKNNE EAEDYDDDLT DSEMDVVRFD DDNSPSFIQI RSVAKKHPKT
      401  *   ******                                                       ↑
********** 
WVHYIAAEEE DWDYAPLVLA PDDRSYKSQY LNNGPQRIGR KYKKVRFMAY TDETFKTREA IQHESGILGP LLYGEVGDTL LIIFKNQASR PYNIYPHGIT
                                                                           501
DVRPLYSRRL PKGVKHLKDF PILPGEIFKY KWTVTVEDGP TKSQPRCLTR YYSSFVNMER DLASGLIGPL LICYKESVDQ RGNQIMSDKR NVILFSVFDE
                                                                           601
NRSWYLTENI QRFLPNPAGV QLEDPEFQAS NIMHSINGYV FDSLQLSVCL HEVAYWYILS IGAQTDFLSV FFSGYTFKHK MVYEDTLTLF PFSGETVFMS
                                                                           701  
                                                                           50kDa', 80kDa
                                                                                         *****
MENPGLWILG CHNSDFRRNG MTALLKVSSC DKNTGDYYED SYEDISAYLL SKNNAIEPRS FSQNSRHPST RQKQFNATTI PENDIEKTDP WFAHRTPMPK
                                                                           801                      ↑
IQNVSSSDLL MLLRQSPTPH GLSLSDLQEA KYETFSDDPS PGAIDSNNSL SENTHFRPQL HHSGDMVFTP ESGLQLRLNE KLGTTAATEL KKLDFKVSST
                                                                           901
SNNLISTIPS DNLAAGTDNT SSLGPSMPV HYDSQLDTTL FCKKSSPLTE SGGPLSLSEE NNDSKLLESC LMNSQESSWG KNVSSTESGR LFKGKRAHGP
                                                                           1001
ALLTKDNALF KVSISLLKTN KTSNNSATNR KTHIDGPSLL IENSPSVWQN ILESDTEFKK VTPLIHDRML MDKNATALRL NHMSNKTTSS KNMEMVQQKK
                                                                           1101
EGPIPPDAQN PDMSFFKMLF LPESARWIQR THGKNSLNSG QGPSPKQLVS LGPEKSVEGQ NFLSEKNKVV VGKGEFTKDV GLKEMVFPSS RNLFLTNLDN
```

TABLE I-continued
Full-length Protein Sequence of Human Factor VIII:c

|  | 1201 |  |  |  |  |  |  |  |
|---|---|---|---|---|---|---|---|---|
| LHENNTHNQE | KKIQEEIEKK | ETLIQENVVL | PQIHTVTGTK | NFMKNLFLLS | TRQNVEGSYE | GAYAPVLQDF | RSLNDSINRT | KKHTAHFSKK | GEEENLEGLG |
| NQTKQIVEKY | AGTTRISPNT | SQQNFVTQRS | | | | | | | |
|  | 1301 | | | | | | | | |
|  |  | | | | | | | | |
| | | | | LEETELEKRI | IVDDTSTQWS | KNMKHLTPST | LTQIDYNEKE | KGAITQSPLS | DCLTRSHSIP |
| QANRSPLPIA | KVSSFPSIRP | IYLTRVLFQD | | | | | | | |
|  |  | 1401 | | | | | | | |
| | | | NSSHLPAASY | RKKDSGVQES | SHFLQGAKKN | NLSLAILTLE | MTGDQREVGS | LGTSATNSVT | YKKVENTVLP |
| KPDLPKTSGK | VELLPKVHIY | QKDLFPTETS | | | | | | | |
|  |  | 1501 | | | | | | | |
| | | | NGSPGHLDLV | EGSLLQGTEG | AIKWNEANRP | GKVPFLRVAT | ESSAKTPSKL | LDPLAWDNHY | GTQIPKEEFK |
| SQEKSPEKTA | FKKKDTILSL | NACESNHAIA | | | | | | | |
|  | 1601 | | | | | | | | |
| 69kDa | | | AINEGQNKPE | IEVTWAKQGR | TERLCSQNPP | VLKRHQREIT | RTTLQSDQEE | IDYDDTISVE | MKKEDFDIYD |
| EDENQSPRSF | QKKTRHYFIA | AVERLWDYGN | | | | | | | |
|   | 1701 |   |   |   |   | 76kDa |   |   |   |
|   |   | | SSSPHVLRNR | AQSCSVPQFK | KVVFQEFTDG | SFTQPLYRGE | LNEHLGLLGP | YIRAEVEDNI | MVTFRNQASR |
| PYSFYSSLIS | YEEDQRQGAE | PRKNFVKPNE | | | | | | | |
|  |  | 1801 | | | | | | | |
| | | | TKTYFWKVQH | HMAPTKDEFD | CKAWAYFSDV | DLEKDVHSGL | IGPLLVCHTN | TLNPAHGRQV | TVQEFALFFT |
| IFDETKSWYF | TENMERNCRA | PCNIQMEDPT | | | | | | | |
|  |  | 1901 | | | | | | | |
| | | | FKENYRFHAI | NGYIMDTLPG | LVMAQDQRIR | WYLLSMGSNE | NIHSIHFSGH | VFTVRKKEEY | KMALYNLYPG |
| VFETVEMLPS | KAGIWRVECL | IGEHLHAGMS | | | | | | | |
|   | 2001 | | | | | | | | |
| | | | TLFLVYSNKC | QTPLGMASGH | IRDFQITASG | QYGQWAPKLA | RLHYSGSINA | WSTKEPFSWI | KVDLLAPMII |
| HGIKTQGARQ | KFSSLYISQF | IIMYSLDGKK | | | | | | | |
|   | 2101 | | | | | | | | |
| | | | WQTYRGNSTG | TLMVFFCNVD | SSGIKHNIFN | PPIIARYIRL | HPTHYSIRST | LFMELMGCDL | NSCSMPLGME |
| SKAISDAQIT | ASSYFTNMFA | TWSPSKARLH | | | | | | | |
|   | 2201 | | | | | | | | |
| | | | LQGRSNAWRP | QVNNPKEWLQ | VDFQKTMKVT | GVTTQGVKSL | LTSMYVKEFL | ISSSQDCHQW | TLFFQNGKVK |
| VFQGNQDSFT | PVVNSLDPPL | LTRYLRIHPQ | | | | | | | |
|   | 2301 | | | | | | | | |
| | | | SWVHQIALRM | EVLGCEAQDL | Y | | | | | tripeptide sequences of the formula asparagine-X-threonine or asparagine-X-serine, where X is generally any amino acid except perhaps proline. Exemplary compounds of this aspect of the invention include variants in which the sequence "NRA" spanning the Factor Xa cleavage site is replaced with of this aspect of the invention containing an engineered N-linked glycosylation site at one or more cleavage sites may additionally contain a modification such as an arginine replacement at one or more other cleavage sites in accordance with the previously-described aspect of the invention. An exemplary compound of this sort contains an Ile substituted for Arg at position 1648 in the 76 kd cleavage site and the sequence NRS or NRT substituted for NRA at the Factor Xa cleavage site (positions 1720–1722).

One subgenus of variants presently preferred include those containing a modification at the 76 kd cleavage site. These variants thus contain an amino acid substitution at Arg-1648 or a consensus N-linked glycosylation site comprising the sequence -NXT- or -NXS- (wherein X is any amino acid, preferably not proline, however) substituted for QRE, or preferably for HQR or REI, the three tripeptide sequences spanning the 76 kd cleavage site. This subgenus includes variants modified only at the 76 kd site, and in addition at one, two, three, four, five, six or all seven other cleavage sites within the purview of this invention and optionally containing Lys instead of Arg at position 1689. For example, this subgenus includes variants in which R-1648 is replaced with another amino acid or E-1649 is replaced with N, which further contain a replacement amino acid for R-1313. This subgenus also includes variants modified at one or more of the proposed APC, 90 kd, 95 kd, 115 kd, 76 kd, 69 kd (lysine substitution only) and Factor Xa cleavage sites.

Also, presently preferred is the subgenus of variants containing modification at both the proposed APC and Xa cleavage sites. This subgenus also includes variants modified at one or more of the other cleavage sites, including preferably the 76 kd site.

Variants in accordance with this invention also include proteins with allelic variations or other amino acid substitutions or deletions which still retain Factor VIII: c-type procoagulant activity.

All variants of this invention may be prepared by expressing recombinant DNA sequences encoding the desired variant in host cells, preferably mammalian host cells, as is known in the art. DNA sequences encoding the variants may be produced by conventional site-directed mutagenesis of DNA sequences encoding human Factor VIII:c or the deletion analogs thereof.

DNA sequences encoding human Factor VIII:c have been cloned. One sequence encoding the full-length human protein of Table I as well as a sequence encoding the deletion analog pDGR-2 have been deposited with the American Type Culture Collection, (ATCC) in Rockville, MD.

Preparation of the full-length human factor VIII:c cDNA has been set forth in detail in U.S. patent applications Ser. Nos. 546,650 (filed Oct. 28, 1983) and 644,086 (filed Aug. 24, 1984). A pSP64 recombinant clone containing the nucleotide sequence depicted in Table I, designated as pSP64-VIII, is on deposit at the American Type Culture Collection under Accession Number ATCC 39812.

To prepare cDNA encoding deletion analogs of Factor VIII:c, restriction endonucleases were used to obtain cleavage of the full-length human factor VIII:c cDNA, at appropriate sites in the nucleotide sequence. Restriction endonucleases are generally utilized under the conditions and in the manner recommended by their commericial suppliers. The restriction endonucleases selected are those which will enable one to excise with substantial specificity sequences that code for the portion of the factor VIII:c molecule desired to be excised. BamHI and SacI are particularly useful endonucleases. However, the skilled artisan will be able to utilize other restriction endonucleases chosen by conventional selection methods. The number of nucleotides deleted may vary but care should be taken to insure that the reading frame of the ultimate cDNA sequence will not be affected.

The DNA sequences encoding the deletion analogs can, in addition to other methods, be derived from the full-length sequence of human factor VIII:c DNA by application of oligonucleotide-mediated deletion mutagenesis, often referred to as "loopout" mutagenesis, as described for example in Morinaga, Y. et al. *Biotechnology*, 2:636–639 (1984).

Deletion analogs containing a deletion of 1–951 amino acids between the 90 kd and 69 kd cleavage sites and methods for their preparation are described in detail in co-assigned U.S. Ser. No. 725,350 (filed Apr. 12, 1985) and International Application No. PCT/US86/00774 (published 23 Oct. 1986 as WO 86/06101), based thereon. Plasmid pDGR-2 which contains cDNA encoding a deletion analog lacking 581 amino acids has been deposited with the American Type Culture Collection as ATCC 53100. Analogous deletion variants containing a deletion of 1–1317 amino acids between Arg-372 (at the 50/40 cleavage site) and Ser-1690 (at the 69 kd cleavage site) can be prepared using the general methods described in PCT/US86/00774, supra. More specifically, a DNA molecule encoding such deletion analogs may be readily prepared from a DNA molecule encoding either full-length Factor VIII or a previous deletion analog such as pDGR-2, by loop-out mutagenesis using appropriate oligonucleotides or appropriate restriction enzymes, as will be readily understood by those of ordinary skill in this art.

By these means one may readily prepare a cDNA encoding a protein having factor VIII:c type procoagulant activity wherein the protein is characterized by amino acid sequence:

In the formula A—X—B, A represents a protein region comprising the polypeptide sequence Ala-1 through Arg-372 of a full-length sequence of factor VIII:c, e.g. substantially as shown in Table I. B represents a protein region comprising the polypeptide sequence Ser-1690 through Tyr-2332 of a full-length sequence of Factor VIII:c, e.g. substantially as shown in Table I. X represents a protein region comprising 0–1316 amino acids substantially duplicative of sequences of amino acids within the sequence Arg-372 through Ser-1690 of a full-length sequence of Factor VIII:c, e.g. substantially as shown in Table I. It should be understood that the amino terminus of X is covalently bonded through a peptide bond to the carboxy terminus of A, and the carboxyl terminus of X is likewise bonded to the amino terminus of B. It should be further understood, however, that where X represents 0 amino acids, the amino terminus of A is covalently bonded by a peptide bond directly to the carboxyl terminus of B, to form an Arg-372-Ser-1690 fusion. Proteins of this invention may be produced by culturing a host cell containing the appropriate cDNA using conventional expression vectors and techniques. Proteins of this invention include, inter alia, proteins of the formula A—X—B wherein X comprises a peptide sequence of 0-367 amino acids substantially duplicative of sequences of amino acids within the sequence Arg-372 through Arg-740 of a full-length sequence of factor VIII:c, e.g., substantially as shown in Table I.

As mentioned above, DNA sequences encoding individual variants of this invention may be produced by conventional site-directed mutagenesis of a DNA sequence encoding human Factor VIII:C or deletion analogs thereof. Such methods of mutagenesis include the M13 system of Zoller and Smith, Nucleic Acids Res. 10:6487-6500 (1982); Methods Enzymol. 100:468-500 (1983); and DNA 3:479-488 (1984), using single stranded DNA and the method of Morinaga et al., Bio/-technology, 636-639 (July 1984), using heteroduplexed DNA. Exemplary oligonucleotides used in accordance with such methods to convert an arginine codon to a codon for isoleucine, for example, are shown in Table II. It should be understood, of course, that DNA encoding each of the proteins of this invention may be analogously produced by one skilled in the art through site-directed mutagenesis using(an) appropriately chosen oligonucleotide(s).

The new DNA sequences encoding the variants of this invention can be introduced into appropriate vectors for expression in mammalian cells. The procoagulant activity produced by the transiently transfected or stably transformed host cells may be measured by using standard assays for blood plasma samples.

TABLE II

Exemplary Oligonucleotides

| No. | Sequence | Mutation |
|---|---|---|
| 1. | GTC TTG AAA CGC CAT CAA ATA GAA ATA ACT CGT ACT ACT | $R_{1648} \rightarrow I$ |
| 2. | CAT CAA ATA GAA ATA | * (1) |
| 3. | CGC CAT CAA CGG AAC ATA ACT CGT ACT ACT | $E_{1649} \rightarrow N$ |
| 4. | CAA CGG AAC ATA AC | * (3) |
| 5. | GCC ATT GAA CCA ATC AGC TTC TCC CAG | $R_{740} \rightarrow I$ |
| 6. | GAA CCA ATC AGC TTC | * (5) |
| 7. | C TTT ATC CAA ATT ATC TCA GTT GCC AAG | $R_{372} \rightarrow I$ |
| 8. | CAA ATT ATC TCA GTT | * (7) |
| 9. | GT CCA GAG GAA CCC CAA CTA AAG ATG AAA AAT AAT GAA GCGG | $R_{336} \rightarrow K$ |
| 10. | CAA CTA AAG ATG AAA | * (9) |
| 11. | GAA AAT CAG AGC CCC AAA AGC TTT CAA AAG AAA AC | $R_{1689} \rightarrow K$ |
| 12. | AGC CCC AAA AGC TTT | * (11) |
| 13. | CAA CGT AGT AAG ATC GCT TTG AAA CAA TTC | $R_{1313} \rightarrow I$ |
| 14. | AGT AAG ATC GCT TTG | * (13) |

*Used for screening mutagenesis event effected with the oligonucleotide indicated in parentheses. Codons for replacement amino acids are underlined. As those skilled in this art will appreciate, oligonucleotides can be readily constructed for use in deleting one or more amino acids or for inserting a different (replacement) amino acid at a desired site by deleting one or more codons or substituting the codon for the desired amino acid in the oligonucleotide, respectively. Other mutagenesis oligonucleotides can be designed based on an approximately 20-50 nucleotide sequence spanning the desired site, with replacement or deletion of the original codon(s) one wishes to change.

The eukaryotic cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., J. Mol. Biol., 159:601-621 (1982); Kaufman, Proc Natl. Acad. Sci. 82:689-693 (1985). Eucaryotic expression vectors useful in producing variants of this invention may also contain inducible promoters or comprise inducible expression systems as are known in the art.

Established cell lines, including transformed cell lines, are suitable as hosts. Normal diploid cells, cell strains derived from in vitro culture of primary tissue, as well as primary explants (including relatively undifferentiated cells such as haematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosmal DNA, and for subsequent amplification of the integrated vector DNA, both by conventional methods, CHO (Chinese Hamster Ovary) cells are presently preferred. Alternatively, the vector DNA may include all or part of the bovine papilloma virus genome (Lusky et al., Cell, 36:391-401 (1984) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines and the like.

Stable transformants then are screened for expression of the procoagulant product by standard immunological or activity assays. The presence of the DNA encoding the procoagulant proteins may be detected by standard procedures such as Southern blotting. Transient expression of the procoagulant genes during the several days after introduction of the expression vector DNA into suitable host cells such as COS-1 monkey cells is measured without selection by activity or immunologic assay of the proteins in the culture medium.

Following the expression of the DNA by conventional means, the variants so produced may be recovered, purified, and/or characterized with respect to pysiochemical, biochemical and/or clinical parameters, all by known methods.

These compounds have been found to bind to monoclonal antibodies directed to human Factor VIII:C and may thus be recovered and/or purified by immunoaffinity chromatography using such antibodies. Furthermore, these compounds possess Factor VIII:C-like procoagulant activity.

The compounds of this invention can be formulated into pharamaceutically acceptable preparations with a parenterally acceptable vehicle and/or one or more excipients in accordance with procedures known in the art.

The pharmaceutical preparations of this invention, suitable for parenteral administration, may conveniently comprise a sterile lyophilized preparation of the protein which may be reconstituted by addition of sterile solution to produce solutions preferably isotonic with the blood of the recipient. The preparation may be presented in unit or multidose containers, e.g. in sealed ampoules or vials. Their use would be analogous to that of human factor VIII, appropriately adjusted for potency.

The invention will be further understood with reference to the following illustrative experimental examples and procedures, which are purely exemplary, and should not be taken as limiting the true scope of the present invention, as described in the claims.

PLASMID DERIVATIONS

The mutagenesis of factor VIII cDNAs was performed directly in the expression plasmid in order to minimize effort in shuffling sequences between different vectors. Generally, the approach taken for mutagenesis was derived from the procedure of Morinaga with modifications. This approach is facilitated by the construction of plasmids which have convenient unique restriction sites in the factor VIII expression plasmid. The following depicts the construction of a factor VIII expression plasmid which has unique Eco RV, HpaI, Cla I and Xba I restriction sites. Plasmid pMT2 may be obtained by EcoRI digestion of pMT2-VWF, which has been deposited with the American Type Culture Collection under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2VIII was then constructed by digesting pMT2 with Eco RV and XbaI, treating the digested DNA with Klenow fragment of DNA polymerase I, and ligating Cla linkers (NEBiolabs, CATCGATG). This removes bases 2171 to 2421 starting from the Hind III site near the SV40 origin of replication and enhancer sequences of pMT2 (the ClaI derivative of pMT2). The factor VIII cDNA was exised from Sp64 VIII with SalI and blunted with T4 DNA polymerase, and EcoRI adapters were added (AATTCCTCGAGAGCT). The EcoRI-adapted factor VIII cDNA was then ligated into the EcoRI site of the ClaI derivative of pMT2. The resultant plasmid is called pMT2 -VIII.

When the full length factor VIII expression plasmid is introduced into COS-1 cells, low levels of factor VIII are obtained. By deletion of a middle region of the factor VIII coding region (See U.S. Ser. No. 725,350 and related PCT application, supra) higher levels of Factor VIII were obtained which had characteristics very similar to the native forms of factor VIII including thrombin activatibility. Thus, the analysis of mutations in factor VIII cleavage sites was facilitated by studying the mutations in these deleted derivatives which are expressed more efficiently. Thus, a deleted form of the factor VIII expression plasmid pMT2VIII was constructed by taking the KpnI (at 1961 in the factor VIII cDNA) to the XbaI site (in the factor VIII cDNA at 7096 base pairs) from pDGR-2 and ligating it into the KpnI-XbaI fragment of pMT2VIII. The final derivative is pMT2-DGR.

MUTAGENESIS

The mutagenesis of specific sites in the factor VIII expression plasmid involves the following steps:

1) The plasmid pMT-DGR was linearized with ClaI, treated with calf intestine phosphatase, and separated on a 0.8% low melting temperature tris-acetate agarose gel. The linearized band was then extracted by adsorption to silica dioxide and eluted in tris-EDTA.

2) A second lot of pMT-DGR was digested with KpnI and XhoI or KpnI and XbaI as indicated below, and separated on a 0.8% low melting temperature agarose gel and extracted as above.

3) One ug of each of these plasmids were mixed and the volume was adjusted to 18 ul and 2.0 ul of 2 N NaOH was added.

4) The mixture was denatured at room temperature for 10 min, then neutralized with 180 ul of a solution which is 0.02 N HCl and 0.1M Tris-HCl pH 8.0.

5) 20 picomoles of phosphorylated mutagenic oligonucleotide was added to 40 ul of the heteroduplex mixture, 6) The mixture was placed in a 68° C. heat block for 90 min. After the incubation the mixture was allowed to slowly cool at room temperature.

7) For each mutagenic reaction, 40 ul of the heteroduplex oligonucleotide mixture was used. The reactions were made 2 mM $MgCl_2$, 1mM beta-mercaptoethanol, 400 uM ATP, 100 uM deoxynucleotide triphosphate, 3-4 units/ul of Klenow fragment of E. coli DNA polymerase I and 400 units/ul of T4 DNA ligase.

8) The reactions were incubated for 10 minutes at room temperature, transferred to 16° C. and incubated overnight.

9) The reaction was terminated by phenol-chloroform extraction and ethanol precipitation, and the resultant pellet was washed with 70% ethanol and resuspended in 10 ul of sterile $H_2O$.

10) DNA was then used to transform competent HB101 or DH-5 bacteria. The ampicillin resistant colonies were screened with $1 \times 10^6$ cpm/ml of a $^{32}$P-labeled screening oligonucleotide in 5× SSC, 0.1% SDS, 5×denhardt's reagent, and 100 ug/ml denatured salmon sperm DNA.

11) The filters were washed with 5× SSC, 0.1% SDS at a temperature 5 degrees below the calculated melting temperature of the oligonucleotide probe.

12) DNA was prepared from positively hybridizing clones and analyzed initially by digestion with different restriction enzymes and agarose gel electrophoresis. DNA was transferred to nitrocellulose and filters were prepared and hybridized to the screening probes in order to ensure the mutagenic oligonucleotide was introduced into the correct fragment.

13) DNA was then retransformed into E. coli and ampicillin resistant colonies were screened for hybridization to the screening oligonucleotide.

14) Final mutations were confirmed by DNA sequencing (Sanger et al., 1977, Proc. Natl. Acad. Sci. USA 74:5463-5467).

EXAMPLE 1

Alteration of the 76 kd cleavage site:

The alteration of specific cleavage sites may be accomplished by changing the basic amino acid on the amino terminal side of a potential cleavage site. Since the choice of amino acid replacement can affect protein folding and/or function the best choices in this regard are conservative alterations. Some proteases, for example thrombin, are very specific for arginine. Thus, alteration of arginine to a lysine may significantly inhibit cleavage. More dramatic modification, for example a change to isoleucine, would guarantee resistance to proteolysis. Since the protease involved in the cleavage of the 76 kd is not known, a change from the arginine at position 1648 to an isoleucine was performed. The mutagenic oligonculeotide was the 39-mer, No. 1 of Table II. The screening nucleotide was the 15-mer, No. 2 of Table II. The mutagenesis was carried out as above with the KpnI-XbaI fragment of pMT2-DGR and the ClaI digested linear form of pMT2-DGR. The resultant mutant was demonstrated to be correct by DNA sequencing (Sanger et al., supra). DNA (pCSM 1648) was prepared by banding in CsCl and used to transfect COS-1 monkey cells as described (Kaufman, PNAS, 1985, 82:689). 60 hr. post transfection, samples of the conditioned media were taken for factor VIII activity assay by the Kabi Coatest chromagenic assay method (Kabi) or the ability to clot factor VIII deficient plasma (Activated Partial Thromboblastin Time, APTT) before and after thrombin activation. Results from the activity assays are shown in Table III. The mutation of the 76 cleavage site did not decrease the activity of factor VIII generated in the conditioned media. In addition, there was no change in the thrombin activation coefficient. In order to demonstrate that the mutation did actually destroy the cleavage site, the transfected cells were labeled with $^{35}$S-methionine for 6 hrs and conditioned media and cell extracts prepared for analysis by immunoprecipitation and SDS-polyacrylamide gel electrophoresis. The results demonstrated that the alteration of Arg to Ile did not affect the synthesis or secretion of the factor VIII variant from the cell. Analysis of the radiolabeled protein after thrombin digestion indicated a normal appearance of the 69 kd, and 50 and 40 kd fragments. However, the predominant factor VIII species produced was a single chain molecule as a result of resistance to cleavage at the 76 site. This result demonstrated that single chain factor VIII is as active as the native molecule. The single-chain Factor VIII:c variants may be advantageous in that they may be produced in more homogeneous form and may have an improved pharmacokinetic profile relative to natural human or other recombinant Factor VIII:c proteins.

EXAMPLE 2

An alternative to the arg-ile change at the 76 kd cleavage site was to introduce an N-linked glycosylation site at asparagine adjacent to the arg in order to attempt to block cleavage. The potential advantage of this alteration is that the resultant protein would have a carbohydrate to potentially block the modified amino acid from provoking an immunologic response. Thus mutagenic oligonucleotide No. 3 of Table II was synthesized. This converted a Gln-Arg-Glu-Ile-Thr sequence to Gln-Arg-Asn-Ile-Thr. The oligonucleotide used for screening for the mutation was the 14-mer. No. 4 of Table II. For this mutation, the mutagenesis was done in the native, not deleted, factor VIII cDNA which was cloned into a single stranded phage M13 vector. The SalI fragment containing the entire factor VIII cDNA was inserted into the Xho I site of the M13 origin vector, pGC2. pGC2 is a plasmid containing ampicillin resistance, an E. coli origin of replication, an M13 origin of replication and a polylinker containing a XhoI site. Other similar, commercially available plasmids may also be used, of course. The phosphorylated (20 pMoles) mutagenic oligonucleotide was annealed in 10 ul with 1 ug of template containing 20 mM Tris-HCl, 10 mM MgCl$_2$, 50 mM NaCl, 1 dithiothreitol, at 65° C. for 10 min. The reaction was slowly cooled and 10 ul of solution B [20 mM Tris-HCl pH 7.5, 10 mM MgCl$_2$, 10 mM dithiothreitol, 1 mM of each nucleotide triphosphate (dATP, dGTP, dCTP, and dTTP), 10 mM ATP, 400 units/ml ligase and 3-4 units/ul of Klenow fragment of DNA polymerase I], incubated 5 min at 23° C. and then incubated overnight at 16° C. The reaction was terminated by phenol-chloroform extraction and ethanol precipitation. The DNA was resuspended in 10 ul of 10 mM Tris-HCl pH 7.5 and lmM EDTA, and 1 ul taken to transform E. coli. HB101.

DNA (CSM-1649) was prepared and transfected into COS-1 cells as above. After transfection of COS-1 cells as before the conditioned media was assayed and found to contain a relatively low level of activity similar to that produced by the wild-type Factor VIII:c cDNA in pMT2.

Analysis of $^{35}$S-methionine labeled protein as above indicated that the addition of the N-linked sugar partially blocked cleavage. The ability Of this particular type of mutation to block cleavage and allow secretion will probably vary from one protein sequence to another depending on the structure of the protein.

EXAMPLE 3

Mutation of the 90 kd cleavage site:

The mutation of the arginine to a isoleucine at position 740 was performed with oligonucleotide No. 5 of Table II. The correct mutations were screened with 15-mer No. 6 of Table II. The mutagenesis was performed with the KpnI-XbaI fragment of pMT2-DGR and the ClaI-digested linear form of pMT2-DGR. The resulting DNA (CSM-740) was prepared and transfected as described above. Samples were assayed as described above and CSM-740 was found to generate less activity than pMT2-DGR. Analysis of $^{35}$S-methionine labeled cell extracts and conditioned media by immunoprecipitation and gel electrophoresis indicated that Factor VIII synthesis, secretion, activity, and thrombin activation were not dramatically modified by alteration of this cleavage site. Close inspection indicated a less efficient level of secretion for CSM-740. Thus, cleavage of the 90 kd cleavage site is not essential for factor VIII activity.

EXAMPLE 4

Mutation of the thrombin cleavage site at 372:

A. The mutagenic oligonucleotide to convert an arginine to an isoleucine at position 372 was oligonucleotide No. 7 of Table II. The oligonucleotide used to identify correct mutations was No. 8 of Table II. The mutagenesis was carried out with the KpnI-XhoI fragment of pMT2-DGR and the claI digested linear form of pMT2-DGR. The resultant plasmid DNA (CSM-372) was prepared and transfected into COS-1 cells as described above. Samples were assayed as above. The results demonstrated that destruction of the 372 cleavage site results in a loss of more than 90% of factor VIII activity. In addition, thrombin treatment does not restore activity. Further analysis indicated that the modified form of factor VIII was properly synthesized and secreted.

B. To produce the K-372 variant, Example 4A may be repeated using analogs of oligonucleotides 7 and 8 of Table II which contain a Lys codon, e.g. AAA, instead of the Ile codon ATC.

EXAMPLE 5

Mutation of the thrombin cleavage site at R-336 (the proposed activated protein C cleavage site):

A. The mutagenic oligonucleotide to convert an arginine to a lysine at position 336 was oligonucleotide No. 9 of Table II. The oligonucleotide used to screen the mutations was No. 10. The mutagenesis was carried out with the KpnI-XhoI fragment of pMT2-DGR and the ClaI digested linear form of pMT2-DGR. The resultant DNA (CSM-336) was prepared, transfected, and resultant samples assayed as above. The results indicate increased activity and a normal thrombin activatability. The modified factor VIII was not affected in its synthesis or secretion. The increased activity may be attributable to loss of inactivation as a result of proposed Xa cleavage in the cobas assay. Thus, this alteration appears to generate a more stable form of factor VIII.

B. To produce the I-336 variant Example 5A was repeated using analogs of oligonucleotides 9 and 10 of Table II which contain an Ile codon, e.g. ATC, instead of the Lys codon AAG. The I-336 variant so produced had similar biological properties to those of the K-336 variant. Additionally, full-length I-336 and K-336 variants were produced and found to possess similar biological properties to those of the corresponding mutant deletion variants.

EXAMPLE 6

Mutation of the 69 kd cleavage site:

A. The oligonucleotide for mutagenesis of the arginine to a lysine was No. 11 of Table II. The screening oligonucleotide was the 15-mer No. 12 of Table II. Mutagenesis was performed with the KpnI-XhoI fragment of pMT2-DGR and the ClaI digested linear form of pMT2-DGR. DNA harboring the correct mutation (CSM- 1689) was prepared and transfected into COS cells. Cells were analyzed as above. Results indicate that mutation of the 69 kd cleavage site results in similar activity to that generated by pMT2-DGR. Thus, our lysine-for-arginine mutation at the 69 kd cleavage site does not destroy Factor VIII:c activity.

B. To produce the I-1689 variant Example 6A was repeated using analogs of oligonucleotides 11 and 12 of Table II which contain an Ile codon, e.g. ATC, instead of the Lys codon AAA. Surprisingly, the I-1689 variant so produced was found to possess less than 90% of the Factor VIII:c activity obtained with pMT2-DGR. Our results suggest that cleavage at the 69 kd site is important in activating the molecule and that substitution of Lys for Arg-1689 does not abolish such cleavage. Furthermore, K-1689 variants may be useful therapeutically, perhaps with delayed onset of Factor VIII:c activity.

Although the majority of these mutations were constructed and analyzed in the deleted form of factor VIII (DGR), the alterations can be made directly with DNA encoding full-length factor VIII or can be reintroduced from mutagenized deletion variant DNA into the full length factor VIII, cDNA by digestion of mutagenized deletion variant DNA and DNA encoding w.t. Factor VIII:c with the appropriate enzymes and ligation of the appropriate fragments to generate the desired plasmids. In addition, a similar approach can be used to introduce multiple mutations into the factor VIII cDNA. In every case tested we have found that results obtained with mutagenized deletion variants were also obtained with the corresponding full-length variants and that the effect of making multiple amino acid substitutions may be additive with respect to the separately observed results for particular amino acid substitutions. Variants containing substituted amino acids at both the proposed APC cleavage site at R-336 and the Xa cleavage site at R-1721 should be particularly stable variants that are resistant to inactivation.

TABLE III

Activity of modified forms of factor VIII expressed in COS-1 cells:

| Mutation | Activity mU/ml | Thrombin Activation |
|---|---|---|
| Experiment 1 | | |
| CSM-336 R-K | 431 | 10-fold |
| CSM-372 R-I | 10 | — |
| CSM-740 R-I | 114 | 10-fold |
| CSM-1648 R-I | 246 | 10-fold |
| pMT2-DGR | 288 | 10-fold |
| Experiment 2 | | |
| CSM-1649 E-N | 196 | 10-fold |
| pMT2VIII | 185 | 10-fold |
| Experiment 3 | | |
| CSM-1689 R-K | 88 | N.T. |
| pMT2-DGR | 103 | N.T. |

N.T. = Not Tested

What is claimed is:

1. A protein having human Factor VIII:c-type procoagulant activity and an amino acid sequence substantially that of human factor VIII:c characterized in that the arginine at one or more of positions 226, 336, 562, 740, 776, 1313, 1648 or 1721 is replaced with an independently selected replacement amino acid.

2. A protein of claim 1, which is further characterized by the replacement of Arg-1689 by lysine.

3. A protein of claim 1, wherein Arg-1648 is substituted with a replacement amino acid.

4. A protein of claim 3, wherein at least one replacement amino acid is Lys.

5. A protein of claim 3, wherein at least one replacement amino acid is a non-basic amino acid.

6. A protein of claim 1, wherein the arginines at positions 226, 336, 562, 740, 776, 1313, 1648, and 1721 are replaced with independently selected replacement amino acids.

7. A protein having Factor VIII:c-type procoagulant activity and an amino acid sequence substantially that of human factor VIII:c, characterized in that a tripeptide sequence encompassing one or more of positions 226, 336, 562, 740, 776, 1313, 1648, or 1721 is replaced with a tripeptide sequence comprising Asn-X-Thr or Asn-X-Ser, wherein X is any amino acid.

8. A protein of claim 6, wherein X is not Arg.

9. A cDNA encoding a protein of claim 1.

10. A cDNA encoding a protein of claim 2.

11. A cDNA encoding a protein of claim 3.

12. A cDNA encoding a protein of claim 4.

13. A cDNA encoding a protein of claim 5.

14. A cDNA encoding a protein of claim 6.

15. A cDNA encoding a protein of claim 7.

16. A cDNA encoding a protein of claim 8.

17. A host cell containing the cDNA of claim 9 operatively linked to an expression control sequence and capable of expressing the protein encoded by the cDNA.

18. A host cell containing the cDNA of claim 10 operatively linked to an expression control sequence and capable of expressing the protein encoded by the cDNA.

19. A host cell containing the cDNA of claim 11 operatively linked to an expression control sequence and capable of expressing the protein encoded by the cDNA.

20. A host cell containing the cDNA of claim 12 operatively linked to an expression control sequence and capable of expressing the protein encoded by the cDNA.

21. A host cell containing the cDNA of claim 13 operatively linked to an expression control sequence and capable of expressing the protein encoded by the cDNA.

22. A host cell containing the cDNA of claim 14 operatively linked to an expression control sequence and capable of expressing the protein encoded by the cDNA.

23. A host cell containing the cDNA of claim 15 operatively linked to an expression control sequence and capable of expressing the protein encoded by the cDNA.

24. A host cell containing the cDNA of claim 16 operatively linked to an expression control sequence and capable of expressing the protein encoded by the cDNA.

25. A pharmaceutical composition for treating or preventing Hemophilia A which comprises an effective amount of a protein of claim 1 in admixture with a parenterally acceptable vehicle or excipient.

26. A pharmaceutical composition for treating or preventing Hemophilia A which comprises an effective amount of a protein of claim 2 in admixture with a parenterally acceptable vehicle or excipient.

27. A pharmaceutical composition for treating or preventing Hemophilia A which comprises an effective amount of a protein of claim 3 in admixture with a parenterally acceptable vehicle or excipient.

28. A pharmaceutical composition for treating or preventing Hemophilia A which comprises an effective amount of a protein of claim 4 in admixture with a parenterally acceptable vehicle or excipient.

29. A pharmaceutical composition for treating or preventing Hemophilia A which comprises an effective amount of a protein of claim 5 in admixture with a parenterally acceptable vehicle or excipient.

30. A pharmaceutical composition for treating or preventing Hemophilia A which comprises an effective amount of a protein of claim 6 in admixture with a parenterally acceptable vehicle or excipient.

31. A pharmaceutical composition for treating or preventing Hemophilia A which comprises an effective amount of a protein of claim 7 in admixture with a parenterally acceptable vehicle or excipient.

32. A pharmaceutical composition for treating or preventing Hemophilia A which comprises an effective amount of a protein of claim 8 in admixture with a parenterally acceptable vehicle or excipient.

* * * * *

UNITED STATES PATENT AND TRADEMARK OFFICE
CERTIFICATE OF CORRECTION

PATENT NO. : 5,451,521

DATED : September 19, 1995

INVENTOR(S) : Kaufman, et al.

Page 1 of 2

It is certified that error appears in the above-indentified patent and that said Letters Patent is hereby corrected as shown below:

At column 3, Table I, line 4, please replace "TRRYYLCAVE" with --TRRYYLGAVE--.
At column 3, Table I, line 4, please replace "VEFTMHLFNI" with --VEFTVHLFNI--.
At column 3, Table I, line 6, please replace "ECHTFLVRNH" with --EGHTFLVRNH--.
At column 3, Table I, line 7, please replace "494kDA" with --40kDA--.
At column 3, Table I, line 9, above the set of letters "DWDYAPLVLA", please delete the asterick (*) above the first letter "L".
At column 3, Table I, line 10, please replace "TKSOPRCLTR" with --TKSDPRCLTR--.
At column 4, Table I, line 14, please replace "SENTHFRPQL" with --SFMTHFRPQL--.
At column 4, Table I, line 15, please replace "FCKKSSPLTE" with --FGKKSSPLTE--.
At column 4, Table I, line 15, please replace "NNDSKLLESC" with --NNDSKLLESG--.
At column 5, Table I continued, line 3, please replace "RSLNDSINRT" with --RSLNDSTNRT--.
At column 5, Table I-continued, line 4, please replace "AGTTRISPNT" with --ACTTRISPNT--.
At column 5, Table I-continued, line 6, please replace "GTQIPKEEFK" with --GTQIPKEEWK--.
At column 5, Table I-continued, line 10, please replace "AVERLWDYGN" with --AVERLWDYGM--.
At column 5, Table I-continued, line 10, please replace "AQSCSVPQFK" with --AQSGSVPQFK--.
At column 6, Table I-continued, line 14, please replace "TLMVFFCNVD" with --TLMVPFGNVD--.
At column 6, Table I-continued, line 14, please replace "LFMELMGCDL" with  LRMELMGCDL--.
At column 6, Table I-continued, line 15, please replace "ISSSQDCHQW" with --ISSSQDGHQW--.
At column 6, Table I-continued, line 16, please replace "LTRYLRJHPQ" with --LTRYLRIHPQ--.
At column 9, Table II, line 40, No. 1, second line, please replace the first "ATA" with --ATA--.
At column 9, Table II, line 42, No. 3, first line, please replace "AAC" with --AAC--.
At column 9, Table II, line 44, No. 5, first line, please replace "ATC" with --ATC--.
At column 9, Table II, line 47, No. 7, first line, please replace the second "ATC" with --ATC--.
At column 9, Table II, line 50, No. 9, second line, please replace "AAG" with --AAG--.
At column 9, Table II, line 53, No. 11, first line, please replace "AAA" with --AAA--.
At column 9, Table II, line 55, No. 13, first line, please replace "ATC" with --ATC--.
At column 10, line 45, please replace "pysiochemical" with --physiochemical--.
At column 10, line 54, please replace "pharamaceutically" with --pharmaceutically--.
At column 12, line 11, please change the comma to a period.

UNITED STATES PATENT AND TRADEMARK OFFICE
CERTIFICATE OF CORRECTION

PATENT NO. : 5,451,521

DATED : September 19, 1995

INVENTOR(S) : Kaufman, et al.

It is certified that error appears in the above-indentified patent and that said Letters Patent is hereby corrected as shown below:

At column 13, line 61, please replace "1 dithiothreitol," with --1 mM dithiothreitol,--.
At column 14, line 3, please replace "1mM" with --1 mM--.
At column 14, line 13, please replace "Of" with --of--.
At column 14, line 46, please replace "claI" with --ClaI--.
At column 14, lines 58/59, please replace "AAA," and "ATC." with --AAA,-- and --ATC.--, respectively.
At column 15, line 4, please replace "activatability" with --activatibility--.
At column 15, lines 12/13, please replace "ATC." and "AAG." with --ATC,-- and --AAG,--, respectively.
At column 15, lines 37/38, please replace "ATC," and "AAA." with --ATC,-- and --AAA,--, respectively.
At column 15, line 53, please delete the comma after the Roman numerals "VIII".

Signed and Sealed this

Ninth Day of July, 1996

Attest:

BRUCE LEHMAN

Attesting Officer

Commissioner of Patents and Trademarks